United States Patent
Fink et al.

(10) Patent No.: US 9,760,554 B2
(45) Date of Patent: *Sep. 12, 2017

(54) INCORPORATING CONTENT ANALYTICS AND NATURAL LANGUAGE PROCESSING INTO INTERNET WEB BROWSERS

(71) Applicant: International Business Machines Corporation, Armonk, NY (US)

(72) Inventors: Patrick W. Fink, Charlotte, NC (US); Kristin E. McNeil, Charlotte, NC (US); Philip E. Parker, York, SC (US); David B. Werts, Charlotte, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 189 days.

This patent is subject to a terminal disclaimer.

(21) Appl. No.: 14/529,517

(22) Filed: Oct. 31, 2014

(65) Prior Publication Data

US 2016/0124927 A1    May 5, 2016

(51) Int. Cl.
G06F 17/00    (2006.01)
G06F 17/24    (2006.01)
G06F 17/27    (2006.01)
G06F 17/30    (2006.01)
G06F 19/00    (2011.01)

(52) U.S. Cl.
CPC ........ *G06F 17/241* (2013.01); *G06F 17/2785* (2013.01); *G06F 17/30684* (2013.01); *G06F 19/324* (2013.01)

(58) Field of Classification Search
CPC .............. G06F 17/241; G06F 17/2785; G06F 17/30684; G06F 19/324
See application file for complete search history.

(56) References Cited

U.S. PATENT DOCUMENTS

2008/0140616 A1 * 6/2008 Encina .............. G06F 17/30864
2008/0270120 A1 * 10/2008 Pestian ............... G06F 17/2785
704/9

(Continued)

FOREIGN PATENT DOCUMENTS

WO    2013100978 A1    7/2013

OTHER PUBLICATIONS

Paolo Ciccarese et al., Open semantic annoatation of scientific publications using DOMEO, Jul. 2011, Journal of Biomedical Semantics, pp. 1-14.*

(Continued)

*Primary Examiner* — Howard Cortes
(74) *Attorney, Agent, or Firm* — Patterson + Sheridan, LLP

(57) ABSTRACT

Techniques disclosed herein describe generating annotations for text content rendered on a web browser. The web browser is configured with a content analytics plug-in configured to receive content to render in the web browser. The content itself includes unstructured text. The content analytics plug-in evaluates the unstructured text using content analytics and natural language processing (NLP) techniques to characterize the meaning of one or more passages in the unstructured text. The content analytics plug-in then generates annotations based on the characterizations to display when the web browser renders the content.

11 Claims, 8 Drawing Sheets

(56) References Cited

U.S. PATENT DOCUMENTS

| | | | |
|---|---|---|---|
| 2009/0192968 A1* | 7/2009 | Tunstall-Pedoe | G06N 5/02 706/47 |
| 2010/0049590 A1* | 2/2010 | Anshul | G06F 17/2785 705/7.32 |
| 2010/0174713 A1* | 7/2010 | Baessler | G06F 17/30905 707/736 |
| 2010/0299589 A1 | 11/2010 | Yamada | |
| 2010/0306307 A1* | 12/2010 | Baessler | G06F 17/30896 709/203 |
| 2011/0144978 A1 | 6/2011 | Tinkler | |
| 2011/0161070 A1* | 6/2011 | Chen | G06F 17/2785 704/9 |
| 2013/0096946 A1* | 4/2013 | Shah | G06Q 50/24 705/3 |
| 2013/0124964 A1* | 5/2013 | Viegas | G06F 17/278 715/230 |
| 2013/0179450 A1* | 7/2013 | Chitiveli | G06F 21/6218 707/737 |
| 2013/0262594 A1* | 10/2013 | Bastide | H04L 67/22 709/206 |
| 2014/0181128 A1* | 6/2014 | Riskin | G06F 17/30684 707/756 |
| 2014/0324541 A1* | 10/2014 | Malik | G06Q 30/0203 705/7.32 |
| 2014/0343925 A1* | 11/2014 | Mankovich | G06F 17/30731 704/9 |
| 2015/0106157 A1* | 4/2015 | Chang | G06F 17/27 705/7.29 |

OTHER PUBLICATIONS

Manuel Fiorelli et al., Computer-aided Ontology Development: an integrated environment, May 22, 2010, A workshop at LREC 2010, Valletta, Malta, pp. 28-35.*
List of IBM Patents or Patent Applications Treated as Related.
Fink et al.: "Incorporating Content Analytics and Natural Language Processing Into Internet Web Browsers"; U.S. Appl. No. 14/691,808, filed Apr. 21, 2015.

* cited by examiner

A diagnosis of [hypertension] is assigned for patients given [ICD codes] [401], [401.1], or [401.9] from two or more visits between 1999 to 2001. Over 90% of such patients are receiving one or more [medications] related to hypertension.

Further, the [diabetes status] of each patient was recorded prior to screening. A diagnosis of [diabetes mellitus] was assigned if the patient had been assigned two or more [ICD-9-CM] code [250.0] codes between 1999 and 2001. Drug treatments included [insulin], and [biguanides].

Some adults who were [hypertensive] and who had not have been diagnosed with [diabetes] were screened for diabetes as part of routine care.

Figure 4B

A diagnosis of [hypertension] is assigned for patients given [ICD codes 401], [401.1], or [401.9] from two or more visits between 1999 to 2001. Over 90% of such patients are receiving one or more [medications] related to hypertension.

Further, the [diabetes status] of each patient was recorded prior to screening. A diagnosis of [diabetes mellitus] was assigned if the patient had been assigned two or more [ICD-9-CM] code [250.0] codes 410 between 1999 and 2001. Drug treatments included [insulin], a [biguanides].

Some adults who were [hypertensive] and who had not have been diagnosed with [diabetes] were screened for diabetes as part of routine care.

425

Non-specific code 2012 ICD-9-CM
Diagnosis Code 250.0
Diabetes mellitus without mention of complication Applies To
Diabetes mellitus without mention of complication or manifestation classifiable to 250.1-250.9
Diabetes (mellitus) NOS

Figure 4C

INCORPORATING CONTENT ANALYTICS AND NATURAL LANGUAGE PROCESSING INTO INTERNET WEB BROWSERS

BACKGROUND

The present invention relates to natural language processing (NLP), and more specifically, to generating content analytics for web content using NLP techniques.

Networked computer systems provide a wealth of unstructured data that is available to users connected to the systems. For example, many users access the Internet for research and informational purposes. For instance, a user may access medical websites using a web browser to learn about various medical conditions and symptoms, diagnoses, and treatments related to those conditions. Continuing the medical website example, the medical field identifies conditions, procedures, terminology, and the like using coding systems. For instance, diagnostic coding systems are currently implemented across the world so that medical organizations (e.g., hospitals, research institutions, etc.) can identify diseases, disorders, and so on, using a standardized code. An example of such a coding system is the International Statistical Classification of Diseases (ICD). Many medical web pages may reference such codes in the text content of the page. For example, a web page that generally describes diabetes may include a reference in the text to an ICD-9 code 250, which refers to diabetes mellitus.

However, one concern is making meaningful use of the information provided by website content. Continuing the previous example of medical websites, although ICD-9 codes allow organizations and health providers to classify and identify medical conditions, ordinary users typically cannot immediately identify a condition based on the code alone. That is, upon reading a webpage and seeing a given code, the user usually has to use a search engine to obtain more information. Further, because many different code sets exist in the medical field, even if an ordinary user was familiar with a particular code set, the user might not know other code sets mentioned in a given page. Again, the user would have to search for the meaning on some other source, such as a search engine or reference text to determine the meaning.

SUMMARY

One embodiment presented herein describes a method for generating annotations for web content rendered by a web browser. The method generally includes receiving web content to render by the web browser. The web content includes unstructured text. The unstructured text is evaluated using one or more natural language processing (NLP) tools to identify one or more passages in the unstructured text determined to have a predicted meaning. Visual indicators are generated for annotations associated with the identified one or more passages. The visual indicators are displayable when the browser renders the web content.

Another embodiment presented herein describes a system having a processor and a memory storing a program which, when executed on the processor, performs an operation for generating annotations for web content rendered by a web browser. The operation itself generally includes receiving web content to render by the web browser. The web content includes unstructured text. The unstructured text is evaluated using one or more natural language processing (NLP) tools to identify one or more passages in the unstructured text determined to have a predicted meaning. Visual indicators are generated for annotations associated with the identified one or more passages. The visual indicators are displayable when the browser renders the web content.

Another embodiment presented herein describes a computer program product including a computer-readable storage medium having computer-readable program code configured to perform an operation for generating annotations for web content rendered by a web browser. The operation itself generally includes receiving web content to render by the web browser. The web content includes unstructured text. The unstructured text is evaluated using one or more natural language processing (NLP) tools to identify one or more passages in the unstructured text determined to have a predicted meaning. Visual indicators are generated for annotations associated with the identified one or more passages. The visual indicators are displayable when the browser renders the web content.

BRIEF DESCRIPTION OF THE SEVERAL VIEWS OF THE DRAWINGS

FIG. 4B illustrates an example of a content analytics plug-in being applied to the example web page illustrated in FIG. 4A, according to one embodiment.

FIG. 4C illustrates an annotation presented by a web browser when a user hovers a cursor over a given boxed word, according to one embodiment.

DETAILED DESCRIPTION

Figure 1:
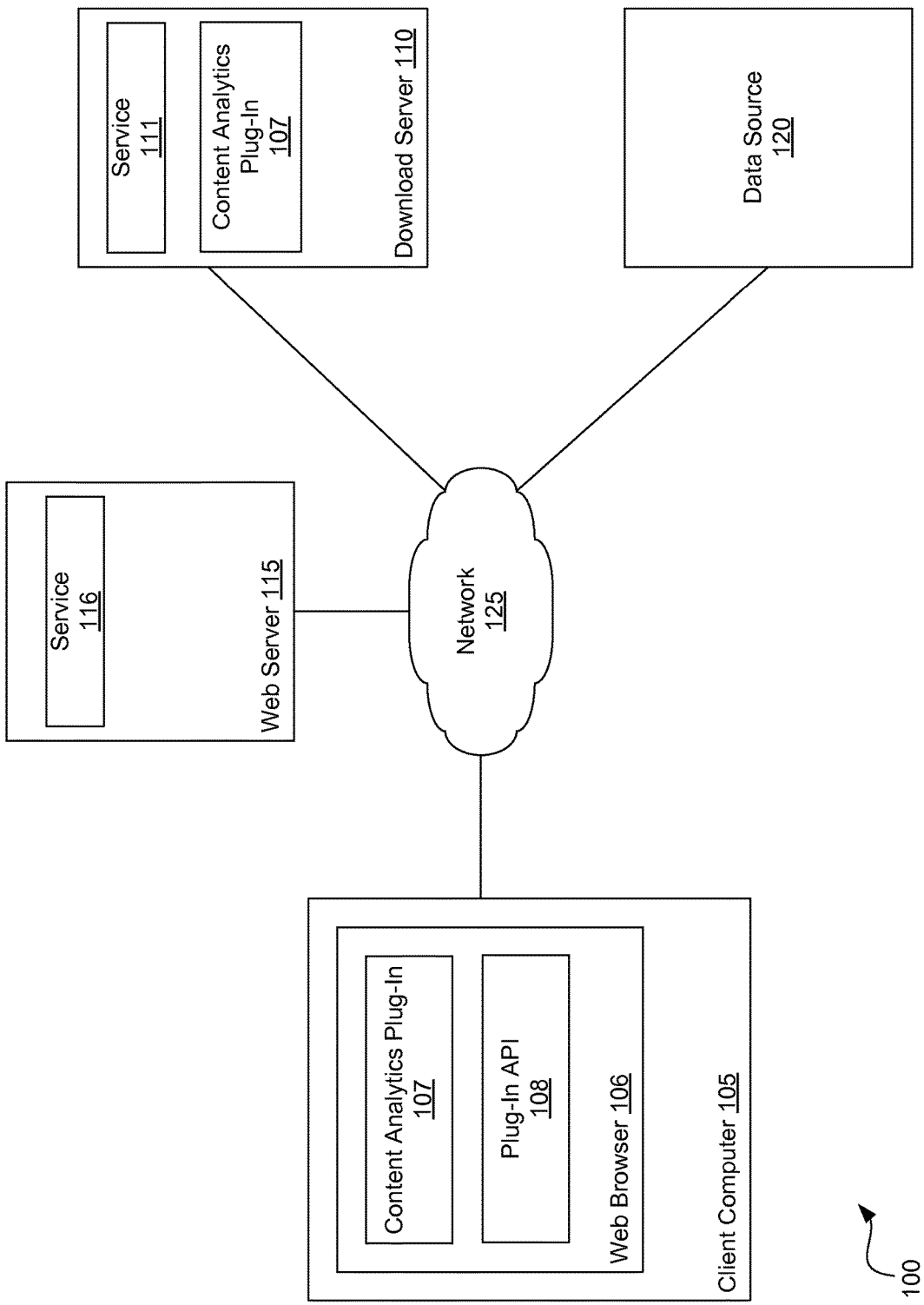
FIG. 1 illustrates an example computing environment, according to one embodiment.

Embodiments presented herein disclose techniques for incorporating content analytics and natural language process (NLP) techniques in a web browser. The NLP techniques are used to provide real-time text analytics and translation capability in web pages rendered by the web browser. More specifically, techniques are described generating content analytics-based annotations for content rendered on a browser. In one embodiment, a web browser includes a content analytics plug-in. The content analytics plug-in provides an NLP framework, such as an Apache Unstructured Information Management Architecture (UIMA) used to process unstructured text data. For example, the content analytics plug-in may include a set of annotators used to generate annotations for passages identified in the unstructured text relating to content domains. As an example, the annotators could analyze unstructured text to identify and annotate for healthcare-related content, e.g., one annotator with a focus on cancer could generate annotations for terms and passages related to cancer, and another annotator can analyze the unstructured text with a focus on diabetes, etc.

Prior to rendering content retrieved from a server, a browser sends web content, including unstructured text, to the content analytics plug-in. The content analytics plug-in processes the text through the NLP framework. The content analytics plug-in generates annotations for passages in the content and modifies the HTML in the web browser such that the annotations are presentable within the web page. For example, the content analytics plug-in may mark analyzed text with a background highlight. When a mouse cursor hovers over the text, the web browser displays the annotation (e.g., in a pop-up window).

Generating annotations using the content analytics plug-in provides a number of advantages. For instance, the content analytics plug-in allows a client to obtain content analytics data for web content in real-time. For example, annotators can parse unstructured text provided in a web page to identify terms to annotate, e.g., medical codes, names of conditions, etc. Further, the annotators can be configured to analyze the unstructured text against local sources. Doing so allows the content analytics plug-in to annotate unstructured text against local data stored on the client machine, providing relative privacy (as opposed to analyzing the text against sources stored on an external network server).

Note, the following references the Netscape Plug-In Application Programming Interface (NPAPI) as an example of an API that provides a translation layer between a content analytics plug-in and a web browser. However, one of ordinary skill in the art will recognize that any plug-in architecture that provides a translation layer between a web browser and a web browser plugin can be used for passing unstructured text from the web browser to the plug-in. Further, the following references the Apache Unstructured Information Management Architecture (UIMA) as an example of an analytical framework for parsing and analyzing unstructured text. One of ordinary skill in the art will recognize that various implementations of UIMA are applicable (Java, C++, etc.), as well as alternative natural language processing architectures (e.g., General Architecture for Text Engineering (GATE)).

Further, the following uses NLP annotators for medical content domains. However, one of ordinary skill in the art will recognize that embodiments presented herein can be adapted for annotators directed to other types of content domains, e.g., legal content domains, content domains relating to entertainment media, etc. For example, a content analytics plug-in can generate annotations to gauge user sentiment in product review websites. The content analytics plug-in can take unstructured text from product reviews hosted on a given website as input and process the text using content analytics and NLP techniques to generate annotations that reflect user sentiment regarding features of a given product. The annotations can indicate features of a product that have generally received positive or negative comments from users (e.g., using colors to indicate positively and negatively received features).

FIG. 1 illustrates an example computing environment 100, according to one embodiment. The computing environment 100 includes a client computer 105. The client computer 105 may be a physical computing system or a virtual machine instance executing in a computing cloud. The client computer 105 includes a web browser 106. The client computer 105 can connect to various servers over a network 125 (e.g., the Internet) via the web browser 106 to access web-based content, e.g., hosted on a web server 115.

The web server 115 provides content (e.g., via a service 116) rendered by web browser 106. The content may include any combination of multimedia (e.g., images, video, etc.) and unstructured text. Based on the unstructured text, a user may desire additional information related to the text. For example, a user may visit a web page related to health risks associated with smoking. The content of the web page may include terminology unfamiliar to the user, such as names of particular narcotics related to smoking, names of diseases associated with smoking, and the like. Normally, the user would have to research each unknown term individually to ascertain the meaning of that term.

In one embodiment, the web browser 106 includes a content analytics plug-in 107, obtained via the network 125 from, e.g., a download server 110 providing a service 111. The content analytics plug-in 107 provides an NLP system, e.g., the UIMA framework, used to analyze the unstructured text based on a variety of configurable annotators added to as part of content rendered on a browser. To do so, a plug-in API 108 serves as an interface between the web browser 106 and the content analytics plug-in 107. That is, the plug-in API 108 provides a translation layer which allows the web browser 106 to send the unstructured text to the UIMA framework provided by the content analytics plug-in 107. The UIMA framework may include successive stages of content analytics or natural language processing of the unstructured text. Each stage includes a particular module used to process the text and pass the processed text on to a next stage for further processing. For example, one stage may execute a module that tokenizes the unstructured text and outputs the tokens to another stage that evaluates frequencies of each word appearing within the text. Further, some of the stages may include an annotator that generates annotations for passages relating to a given content domain. A user may specify which annotators to enable. For example, annotators can be available for content domains related to medical conditions. As such, the user can enable annotators focused on a cancer content domain, diabetes content domain, etc.

Each annotator generates annotations for the text based on one or more data sources 120. Once generated, the web browser 106 renders the content as well as annotations displayed to a user. For example, the web browser 106 may mark text associated with a given annotation to convey that the annotation is available. Further, when a user hovers a mouse cursor over the word, the web browser 106 can open display the annotation.

A data source 120 is a corpus of data, e.g., from dictionaries, online encyclopedias, informational websites, etc. A data source 120 can be hosted on a server connected to the network 125. Further, a data source 120 can also be a collection of data hosted on multiple servers. In addition, a data source 120 can be maintained on the client computer 105. In each case, the annotators analyze unstructured text from web content based on information and data provided by the data sources 120.

As stated, a user can specify content domains for the annotators to monitor and analyze within the text. For example, the user can enable an annotator that generates annotations for terms or passages related to cancer in the text. As a result, when the web browser 106 accesses a given web page, the annotators enabled by the user parse the unstructured text to identify relevant terms or passages related to the subject of cancer, e.g., medical codes, symptoms, diagnoses, treatments, and the like. The annotator can then generate annotations for each of the identified terms or passages based on information in the data sources 120.

Figure 2:
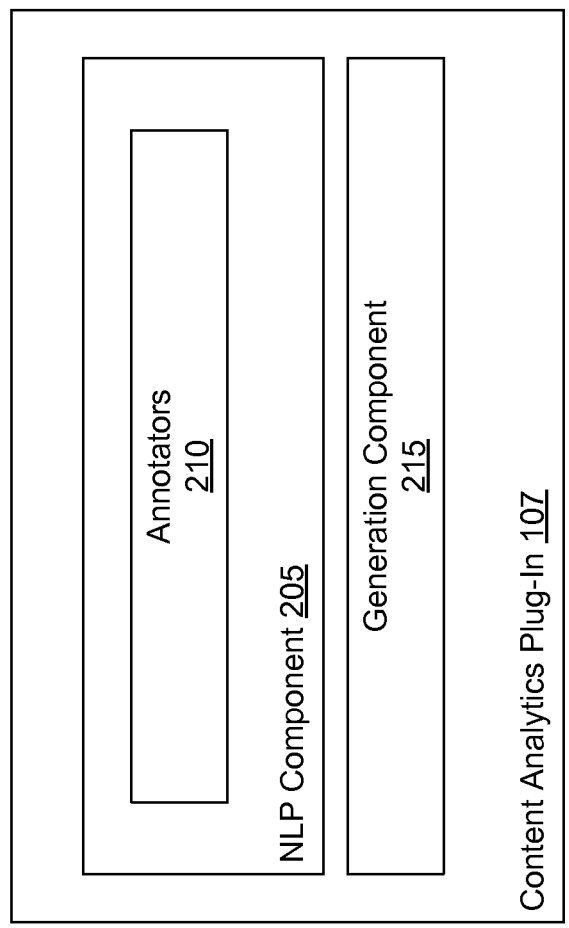
FIG. 2 further illustrates the content analytics plug-in described relative to FIG. 1, according to one embodiment.

FIG. 2 further illustrates the content analytics plug-in 107, according to one embodiment. As shown, the content analytics plug-in 107 includes an NLP component 205 and a generation component 215. In one embodiment, the NLP component 205 is modeled on the UIMA framework. The NLP component 205 receives unstructured text from the web browser 106 via a translation layer provided by the plug-in API 108. The UIMA framework processes the unstructured text at a number of stages using various NLP techniques, e.g., ascertaining meanings of relevant words in the text, generating word clouds of frequently used words, etc. The stages may be successive, i.e., the result of a given stage may be output to the next stage. Further, a stage can be associated with an annotator 210. As stated, the annotators generate annotations for terms related to a given content domain (e.g., cancer, diabetes, pregnancy complications, etc.) based on data sources 120.

In one embodiment, the generation component 215 formats annotations for display in a web browser 106. The generation component 215 manipulates the original web content to include the formatted annotations. For example, the generation component 215 can mark annotated words located in the unstructured text. The generation component 215 exports the annotations and modified web content to the web browser 106. The web browser 106, in turn, can present annotations based on the modifications made by the generation component 215. For example, the web browser 106 can highlight the marked text to indicate to a user terms that are associated with generated annotations. For example, when a user hovers a mouse cursor over the highlighted text, the web browser can display the annotation, e.g., through a pop-up in the browser.

Figure 3:
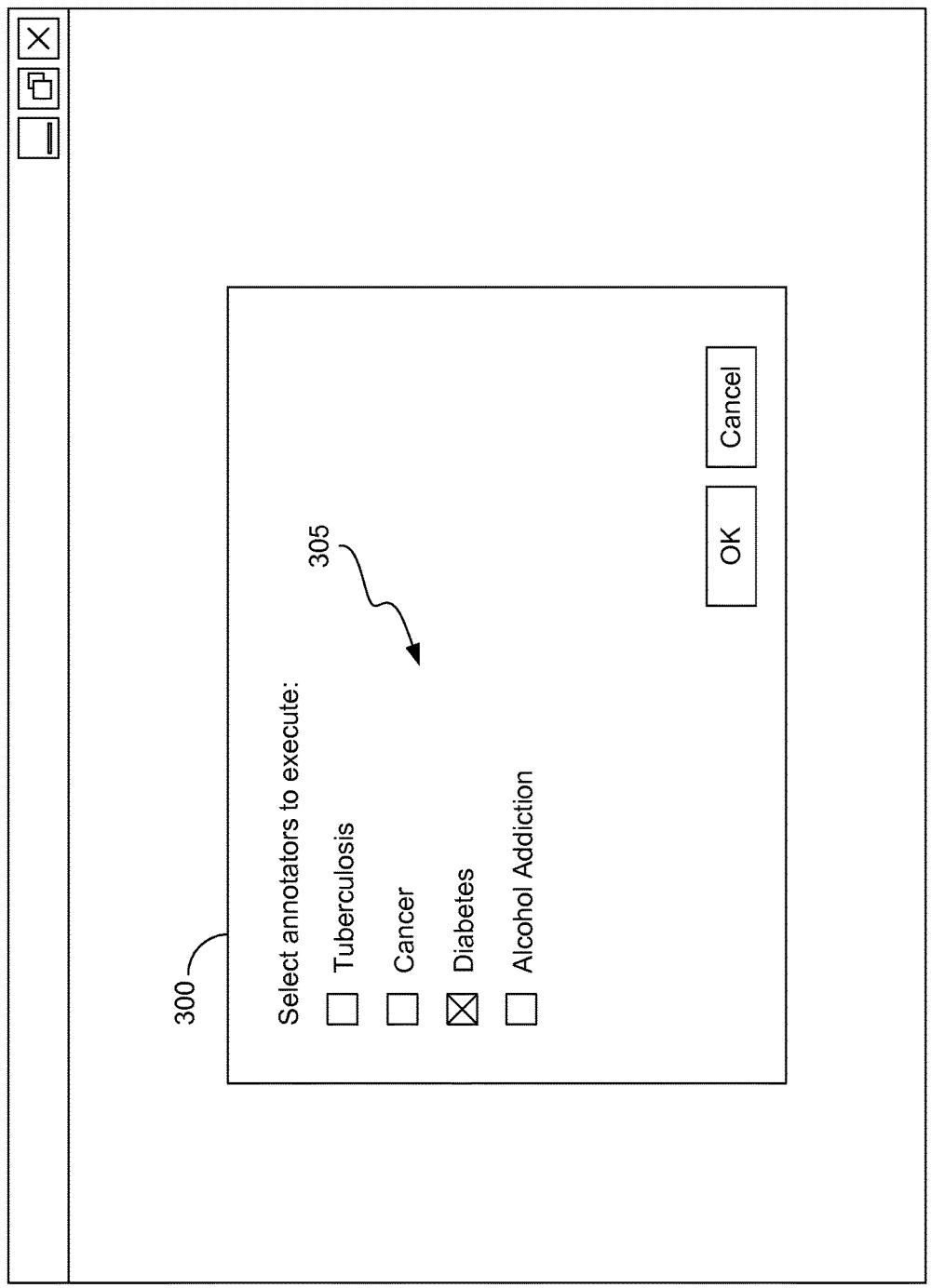
FIG. 3 illustrates an example configuration interface for a content analytics plug-in, according to one embodiment.

FIG. 3 illustrates an example configuration interface 300 for the content analytics plug-in 107, according to one embodiment. Once downloaded to the client computer system 105, a user can configure the content analytics plug-in 107 (e.g., via the web browser 106) to enable or disable annotators provided by the content analytics plug-in 107. For example, the configuration interface 300 provides a listing of medical annotators 305. The medical annotators 305 include annotators related to specific content domains, such as tuberculosis, cancer, diabetes, and alcohol addiction. Of course, the content domains listed in the interface 300 serve as examples. Annotators for various content domains may also be used. Further, the content analytics plug-in 107 may allow users to download additional annotators or remove specified annotators from the plug-in 107.

When enabled, the annotators generate annotations related to an associated content domain. For example, in the interface 300, the annotator for diabetes is enabled. Thus, when a user accesses a particular web page, the plug-in API 108 invokes the content analytics plug-in 107 and passes the unstructured text from the content of the web page into the plug-in 107. The content analytics plug-in 107 passes text to the UIMA framework. The diabetes and generates annotations based on words relating to diabetes in the text. For example, the annotator may identify medical codes, symptoms, treatments, and the like, as relating to diabetes. The annotator may then generate annotations for passages based on data sources 120. For example, one annotator could generate an annotation for a medical code that relates the code to a diagnostic condition and provide a description of the diagnostic condition itself. Once generated, the web browser 106 can then present the annotations to the user. As stated, the annotations can be presented as a pop-up whenever a user hovers over annotated text.

Figure 4A:
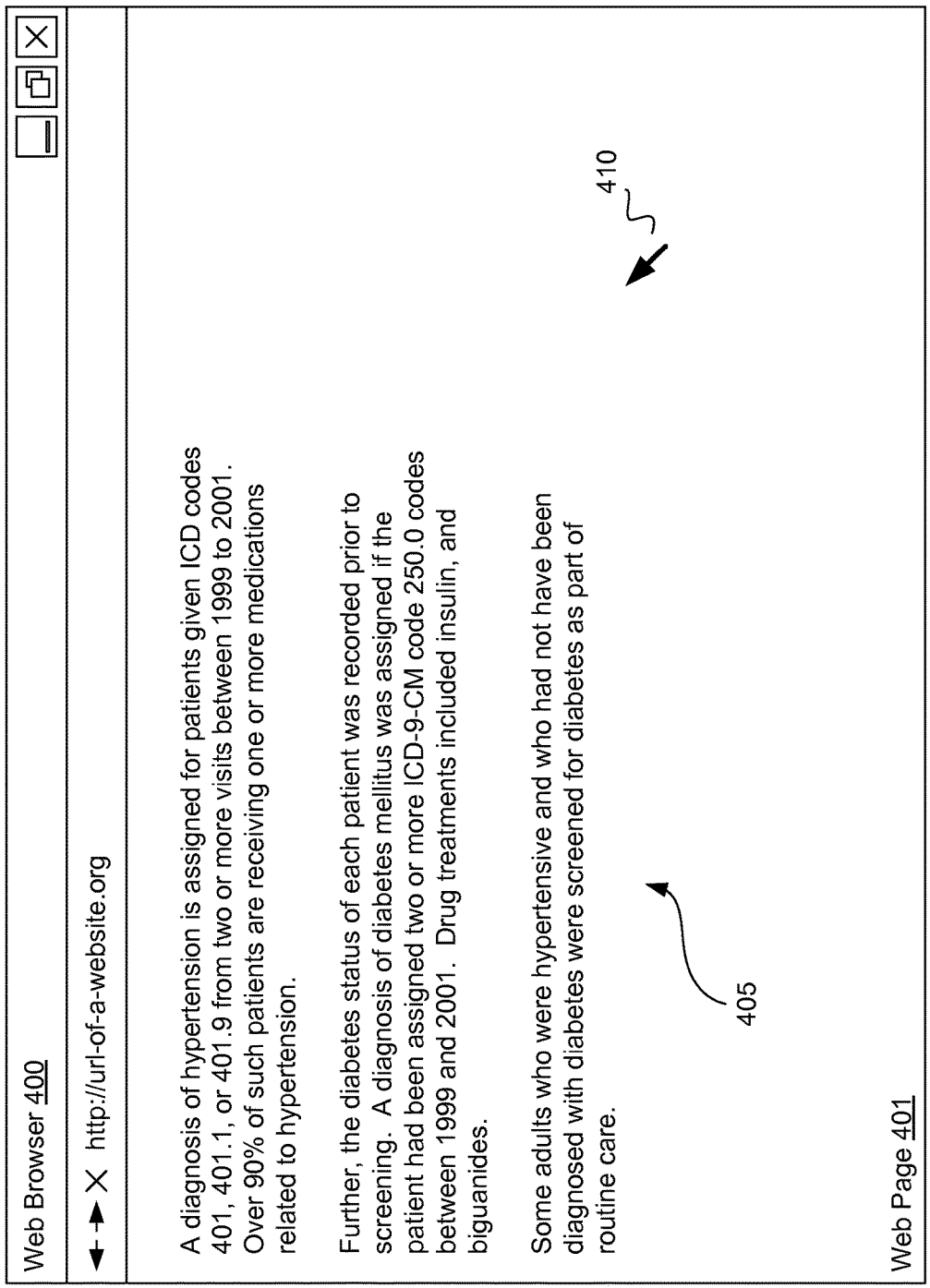
FIG. 4A illustrates an example web page, according to one embodiment.

FIG. 4A illustrates an example web page 401 presented in a web browser 400, according to one embodiment. The web page presents content, shown as text 405. Illustratively, the text 405 describes a medical study conducted on a set of patients. The text 405 includes terminology that may be unfamiliar to a layperson viewing the web page. For example, the text 405 specifies medical codes 401, 401.1, 401.9, and 250.0, without any description about what those particular codes correspond to. A user would have to look-up the codes separately in a database or search engine (e.g., by using cursor 410 to highlight the codes, copy the codes, and paste the codes to a search engine field) to identify the meanings of the codes (and presumably help inform the user whether the codes were relevant to the user). Further, the text 405 also includes medical terminology that might not widely understood, such as "mellitus" or "guanides."

FIG. 4B illustrates an example of the web page 401 after the content analytics plug-in 107 has processed text content of the page, according to one embodiment. For this example, assume a user has enabled a diabetes-focused annotator within the content analytics plug-in 107. As a result, when the user accesses the web page, the plug-in API 108 invokes the content analytics plug-in 107 and passes the text to the NLP component 205. The NLP component 205 performs content analytics and NLP techniques on the text input. Further, the diabetes annotator identifies words related to diabetes in the text and generates annotations for those words. The web browser 106 renders the web content and the generated annotations to be presented to a user. Illustratively, terms related to diabetes are marked with boxes 420 in the web page 401 presented by the web browser 400. For example, conditions such as "hypertension" and "diabetes mellitus" are enclosed by the boxes 420. In addition, medical codes such as ICD codes 401, 401.1, and 401.9 are also enclosed by the boxes 420.

FIG. 4C illustrates an example annotation presented by the web browser 400 when a user hovers the cursor 410 over a given boxed word, according to one embodiment. Illustratively, the cursor 410 is hovered over the boxed term "250.0." In turn, the web browser presents an annotation 425 that provides more information regarding the term "250.0." The information indicates that "250.0" relates to an ICD-9-CM code for diabetes mellitus.

Figure 5:
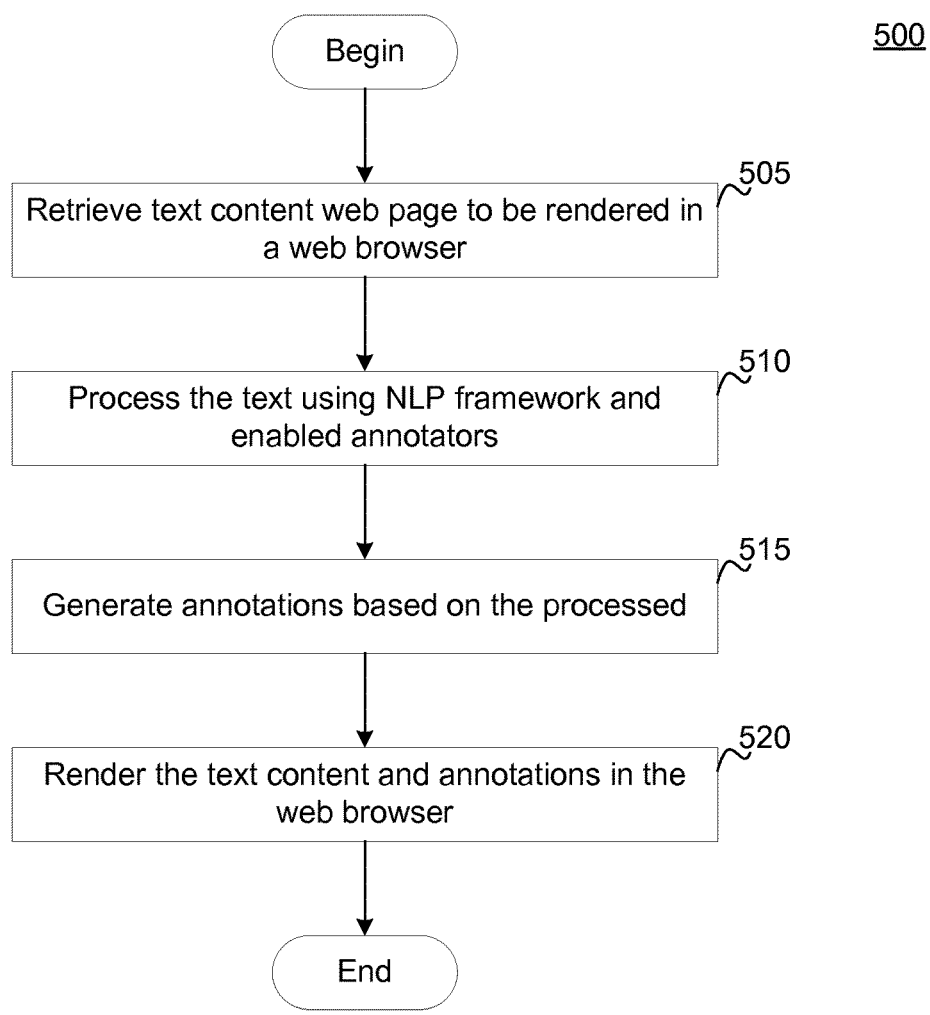
FIG. 5 illustrates a method for generating content analytics annotations for text content rendered in a web browser, according to one embodiment.

FIG. 5 illustrates a method 500 for generating content analytics annotations for text content rendered in a web browser, according to one embodiment. Method 500 begins at step 505, where the content analytics plug-in 107 receives text content of a web page via the plug-in API 108. That is, when a user accesses a web page, prior to the web browser rendering the page content, the plug-in API 108 invokes the content analytics plug-in 107 and passes the unstructured text of the web page as input.

At step 510, the NLP component 205 processes text through successive stages of the UIMA framework. Each stage provides a separate process performed on the unstructured text, e.g., tokenization, lexical analysis, etc. The results of each stage (i.e., resulting tokens, analyzed terms, etc.) can be passed onto successive stages for further processing. Further, as stated, a stage can be associated with an enabled annotator used to generate annotations related to a given content domain, e.g., cancer, pregnancy complications, diabetes, obesity, and the like. For example, assume that a user has enabled a cancer annotator. The annotator may then process the text to identify terms and passages related to cancer, such as medical codes, treatment vocabulary, timelines, and the like. The annotator may also identify words commonly appearing in the text.

At step 515, the NLP component 205 generates annotations based on the processed text and enabled annotators. For example, the NLP component 205 may do so by retrieving information from data sources 120 using the identified words as input. The generation component 210 may then format the annotations for presentation on a web page, e.g., by generating web page code containing the annotations and modifying existing web page code. The generation component 210 may output the formatted annotations to the plug-in API, which in turn sends the annotations and modified web page code to the web browser.

At step 520, the web browser 106 renders the text content and annotations. The web browser 106 may mark terms within the text content that have corresponding annotations. For example, web browser 106 can mark the terms with a colored highlight. Terms annotated by one annotator may be highlighted with a given color, while terms annotated by another annotator may be highlighted with a different color. A user can hover a mouse cursor over a marked term to view a given annotation.

Figure 6:
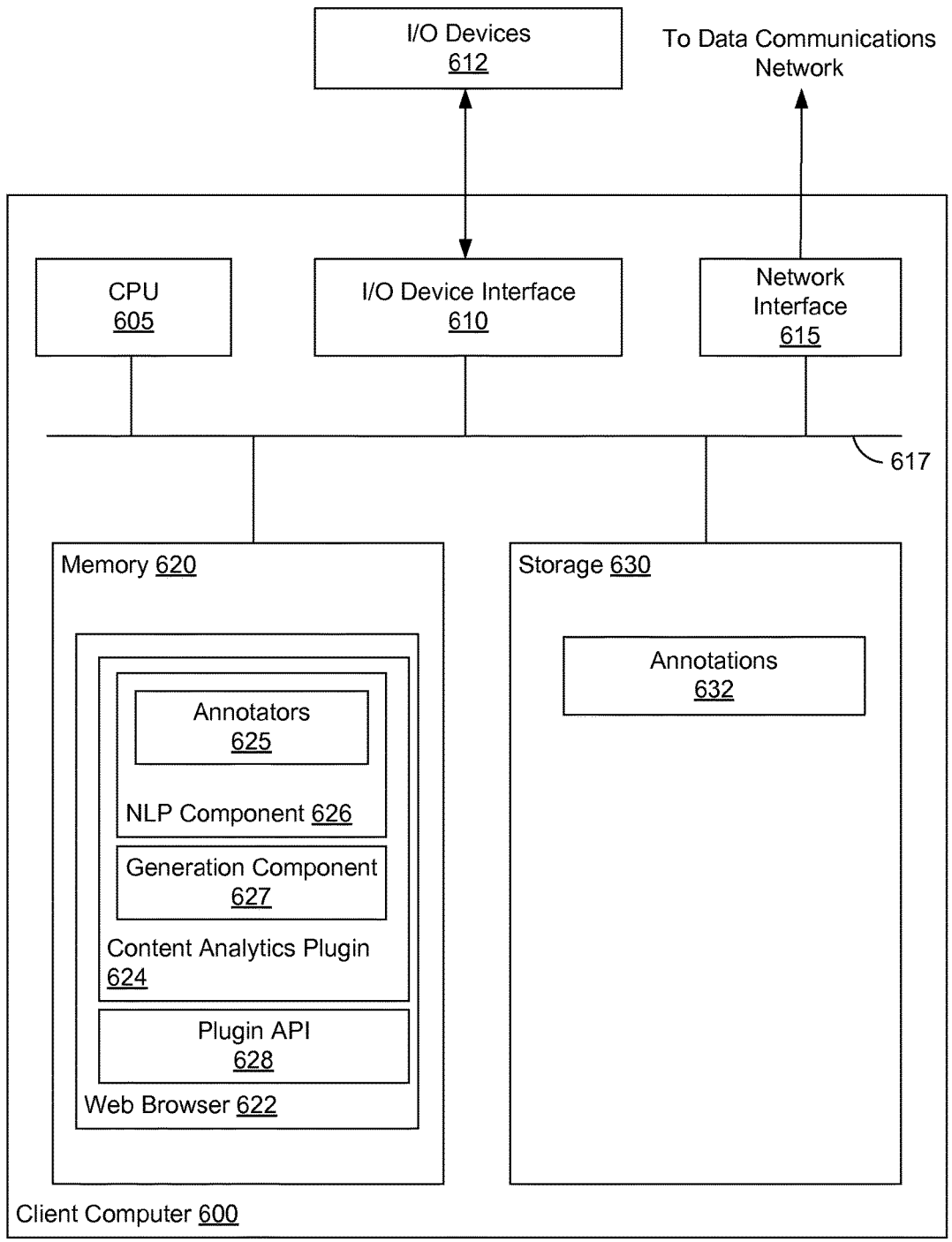
FIG. 6 illustrates an example client computing system, according to one embodiment.

FIG. 6 illustrates an example client computing system 600, according to one embodiment. As shown, the client computing system 600 includes, without limitation, a central processing unit (CPU) 605, a network interface 615, a memory 620, and storage 630, each connected to a bus 617. The client computing system 600 may also include an I/O device interface 610 connecting I/O devices 612 (e.g., keyboard, display and mouse devices) to the client computing system 600. Further, in context of this disclosure, the computing elements shown in the client computing system 600 may correspond to a physical computing system (e.g., a system in a data center) or may be a virtual computing instance executing within a computing cloud.

CPU 605 retrieves and executes programming instructions stored in memory 620 as well as stores and retrieves application data residing in the storage 630. The bus 617 is used to transmit programming instructions and application data between CPU 605, I/O devices interface 610, storage 630, network interface 617, and memory 620. Note, CPU 605 is included to be representative of a single CPU, multiple CPUs, a single CPU having multiple processing cores, and the like. Memory 620 is generally included to be representative of a random access memory. Storage 630 may be a disk drive storage device. Although shown as a single unit, storage 630 may be a combination of fixed and/or removable storage devices, such as fixed disc drives, removable memory cards, or optical storage, network attached storage (NAS), or a storage area-network (SAN).

Illustratively, memory 620 includes a web browser 622. And storage 630 includes annotations 632. The web browser 622 generally renders web content accessed over a network for display to a user. The web browser 622 further includes a content analytics plug-in 624 and a plug-in API 628. The content analytics plug-in 624 generates annotations for unstructured text within web content. When the user accesses a given web page, prior to the web browser 622 rendering the content, the plug-in API 628 invokes the content analytics plug-in 624.

The content analytics plug-in 624 further includes an NLP component 624 and a generation component 627. The NLP component provides a processing framework, such as UIMA, that analyzes the unstructured text using various content analytics and NLP techniques. The NLP component 624 itself includes one or more annotators 625. Each annotator creates annotations in-memory for a given content domain by identifying terms in the unstructured text relating to the content domain. The annotator can retrieve data from a data source for content relating to each of the identified terms. The generation component 627 formats the annotations to conform with the web page content accessed by the web browser. Further, the generation component 627 sends the annotations to the web browser 622, via the plug-in API 628, for rendering. In one embodiment, the annotation can optionally be stored in storage 630 (as annotations 632).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, the content analytics plug-in 107 could access resources available in the cloud, e.g., UIMA framework modules and other NLP processing tools, to perform more complex evaluations on unstructured text of a web page. As another example, the content analytics plug-in 107 could evaluate the unstructured text against data sources provided by the cloud, e.g., dictionaries, encyclopedias, bibliographies, and the like.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A system, comprising:
    a processor; and
    a memory storing a program, which, when executed on the processor, performs an operation for generating annotations for web content rendered by a web browser, the operation comprising:
        receiving, via a plug-in executing in the web browser, input specifying a first annotator of an Unstructured Information Management Architecture (UIMA) that provides a plurality of processing stages, wherein the first annotator is of a plurality of annotators, wherein each annotator is associated with a respective distinct content domain and is configured to, in one of the processing stages, generate annotations associated with the associated distinct content domain for text passages,
        receiving web content to render by the web browser, wherein the web content includes unstructured text,
        evaluating by the first annotator, the unstructured text in one or more of the plurality of processing stages to identify one or more passages in the unstructured text determined to have a predicted meaning within the distinct content domain associated with the first annotator,
        generating, in one or more of the processing stages by the first annotator, annotations for the identified one or more passages within the distinct content domain associated with the first annotator,
        generating visual indicators for the annotations for the identified one or more passages within the distinct content domain associated with the first annotator, and
        modifying the received web content to include the received web content, wherein the visual indicators are displayed when the browser renders the received web content.

2. The system of claim 1, wherein the annotations for each distinct content domain are rendered in a distinct visual indicator.

3. The system of claim 2, wherein the distinct content domains are each based on medical conditions.

4. The system of claim 1, wherein the operation further comprises, rendering the content and the annotations in the web browser.

5. The system of claim 4, wherein the operation further comprises:
    during the rendering of the content and the annotations in the web browser, marking the one or more passages of the content that correspond to each of the annotations.

6. The system of claim 5, wherein the operation further comprises, upon receiving an indication that one of the marked passages is accessed in the web browser, generating a presentation of the corresponding annotation to display in the web browser.

7. A computer program product, comprising:
    a non-transitory computer-readable storage medium having computer-readable program code embodied therewith, the computer-readable program code configured to perform an operation for generating annotations for web content rendered by a web browser, the operation comprising:
        receiving, via a plug-in executing in the web browser, input specifying a first annotator of an Unstructured Information Management Architecture (UIMA) that provides a plurality of processing stages, wherein the first annotator is of a plurality of annotators, wherein each annotator is associated with a respective distinct content domain and is configured to, in one of the processing stages, generate annotations associated with the associated distinct content domain for text passages, receiving web content to render by the web browser, wherein the web content includes unstructured text, evaluating by the first annotator, the unstructured text in one or more of the plurality of processing stages to identify one or more passages in the unstructured text determined to have a predicted meaning within the distinct content domain associated with the first annotator, generating, in one or more of the processing stages by the first annotator, annotations for the identified one or more passages within the distinct content domain associated with the first annotator, generating visual indicators for the annotations for the identified one or more passages within the distinct content domain associated with the first annotator, and modifying the received web content to include the received web content, wherein the visual indicators are displayed when the browser renders the received web content.

8. The computer program product of claim 7, wherein the annotations for each distinct content domain are rendered in a distinct visual indicator.

9. The computer program product of claim 7, wherein the operation further comprises, rendering the content and the annotations in the web browser.

10. The computer program product of claim 9, wherein the operation further comprises:
during the rendering of the content and the annotations in the web browser, marking the one or more passages of the content that correspond to each of the annotations.

11. The computer program product of claim 10, wherein the operation further comprises, upon receiving an indication that one of the marked passages is accessed in the web browser, generating a presentation of the corresponding annotation to display in the web browser.

* * * * *